United States Patent [19]

Carlhoff et al.

[11] Patent Number: 4,995,723
[45] Date of Patent: Feb. 26, 1991

[54] METHOD AND APPARATUS FOR OPTICALLY COUPLING AN ELEMENT ANALYSIS SYSTEM AND A LASER TO LIQUID METAL IN A MELTING VESSEL

[75] Inventors: Christoph Carlhoff, Willich; Claus-Jürgen Lorenzen, Essen; Klaus-Peter Nick, Achim, all of Fed. Rep. of Germany

[73] Assignee: Fried. Krupp Gesellschaft Mit Beschränkter Haftung, Essen, Fed. Rep. of Germany

[21] Appl. No.: 414,387

[22] Filed: Sep. 29, 1989

[30] Foreign Application Priority Data

Oct. 3, 1988 [DE] Fed. Rep. of Germany ....... 3833621

[51] Int. Cl.$^5$ .................... G01J 3/443; G01N 21/63
[52] U.S. Cl. .................................................. 356/318
[58] Field of Search ............................... 356/317, 318

[56] References Cited

U.S. PATENT DOCUMENTS 4,818,106 4/1989 Koch et al. ................... 356/318

FOREIGN PATENT DOCUMENTS 3413589 10/1985 Fed. Rep. of Germany .

Primary Examiner—Vincent P. McGraw
Attorney, Agent, or Firm—Spencer & Frank

[57] ABSTRACT

A method of analyzing elements of a metal melt contained in a melting vessel comprises the following steps: introducing an inert gas at a temperature in excess of 300° C. laterally into a tube passing through a lateral wall of the melting vessel and opening thereinto; generating a laser beam; passing the laser beam through an adjustable first lens system; reflecting the laser beam by a mirror into the tube; guiding the laser beam through a quartz window which closes the tube; generating a plasma in the tube by focusing the laser beam by the adjustable first lens system onto the surface of the metal melt in the tube; guiding the light generated by the plasma through the quartz window to an adjustable second lens system; coupling the light by the adjustable second lens system with an optical waveguide; and introducing the light by the optical waveguide into a spectrometer.

7 Claims, 1 Drawing Sheet

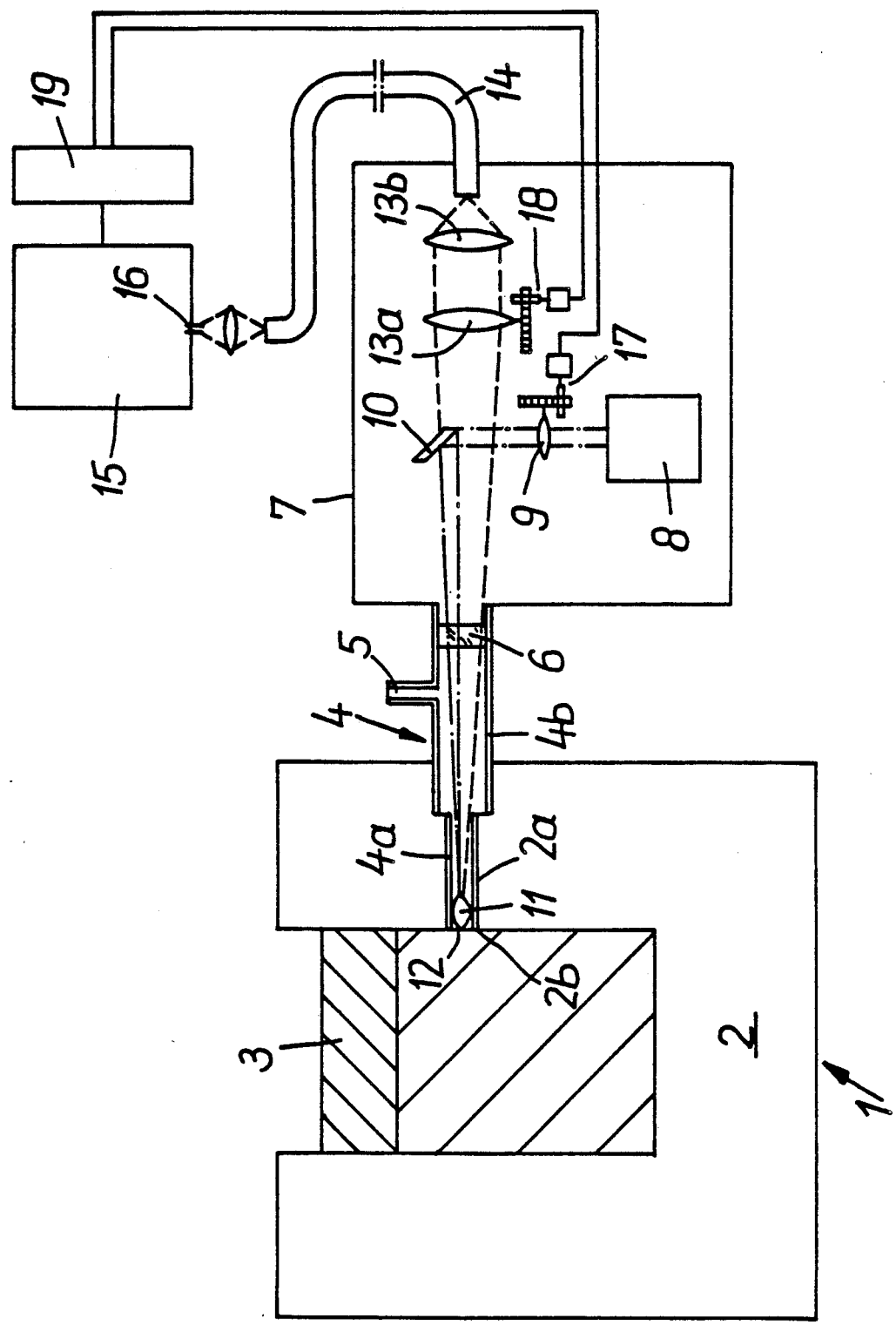

4,995,723

METHOD AND APPARATUS FOR OPTICALLY COUPLING AN ELEMENT ANALYSIS SYSTEM AND A LASER TO LIQUID METAL IN A MELTING VESSEL

CROSS REFERENCE TO RELATED APPLICATION

This application claims the priority of Federal Republic of Germany Application No. P 38 33 621.9 filed Oct. 3rd, 1988, which is incorporated herein by reference.

BACKGROUND OF THE INVENTION

The present invention relates to a method and an apparatus for optically coupling an element analysis system based on laser-induced emission spectrum analysis to the liquid metal in a melting vessel. A direct access to the slag-free metal bath is effected through a bore in the side wall of the vessel below the bath level or in the vessel bottom. To prevent liquid metal from escaping, a gas is blown in so as to produce the necessary counterpressure. A laser beam is focused on the surface portion of the melt at the end of the bore and at that location produces a plasma which emits a radiation specific for the elements present in the plasma. The radiation is directed through the bore onto a spectrograph for a spectral separation.

A method of the above-outlined type is disclosed, for example, in German Offenlegungsschrift (non-examined published application) No. 3,413,589, according to which an inert gas is employed as the gas to produce the necessary counterpressure. This prior art method has a number of disadvantages. Thus, it is difficult to adjust the flow rate of the gas such that the opening of the bore will never freeze shut. The metal surface at the bore must therefore be constantly monitored. The optical coupling of the laser and the spectrometer cannot be optimized if the wall thickness of the melting vessel undergoes reduction. As the wall thickness decreases, the laser beam is no longer focused on the surface of the metal and the excitation temperature drops. With decreasing wall thickness of the melting vessel, the aperture of the bore can no longer be optimally utilized for the emitted light: the image for the emitted light is not sharp, the light yield is reduced and the spectrum will be untrue. Moreover, additional problems occur in the prior art method due to unavoidable micromovements of the melting vessel (shocks and the like) being transferred to the spectrometer. This causes, for example, further deterioration in the intensities and halfwidth values of the spectral lines.

SUMMARY OF THE INVENTION

It is an object of the invention to provide an improved method of the above-outlined type with which the discussed disadvantages are avoided and an apparatus for performing the method.

This object and others to become apparent as the specification progresses, are accomplished by the invention, according to which, briefly stated, the method comprises the following steps: introducing an inert gas at a temperature in excess of 300° C. laterally into a tube passing through a lateral wall of the melting vessel and opening thereinto; generating a laser beam; passing the laser beam through an adjustable first lens system; reflecting the laser beam; passing the laser beam through an adjustable first lens system; reflecting the laser beam by a mirror into the tube; guiding the laser beam through a quartz window which closes the tube; generating a plasma in the tube by focusing the laser beam by the adjustable first lens system onto the surface of the metal melt in the tube; guiding the light generated by the plasma through the quartz window to an adjustable second lens system; coupling the light by the adjustable second lens system with an optical waveguide; and introducing the light by the optical waveguide into a spectrometer. The focusing condition is met if the relation $Me_I/Me_{II}$ is a minimum, whereby $Me_I$ is the intensity of an atomic line of a metal of the melt and $Me_{II}$ is an ionic line of the same metal. The second lens system is adjusted to focus the image of the plasma at the input end of the optical waveguide.

Thus, according to the invention, an inert gas at a temperature of more than 300° C., preferably above 500° C., is fed into the bore and the bore is provided with a tube which is externally closed by a quartz window and is provided with a lateral inlet for the gas. Laser light, emitted by a laser beam generator situated in a housing is directed through the quartz window onto the metal surface where the laser light generates a plasma whose light is applied to the spectrometer. The quartz window is oriented toward the housing which is connected with the tube. The light emitted by the metal surface is conducted to the external spectrometer in an optical waveguide which substantially prevents the transfer of movements of the melting vessel to the spectrometer. Lens system and deflection mirrors are also disposed in the interior of the housing. The deflection mirrors are adjusted in such a way that, on the one hand, the aperture of the optical waveguide is utilized optimally and, on the other hand, the laser beam is focused on the metal surface in the bore and the plasma is focused on the input end of the waveguide. The lens system for the laser light and the plasma light can be adjusted such that refocusing may be effected as the wall thickness of the melting vessel undergoes reduction.

The focusing condition for the laser light is met, if the relation $Me_I/Me_{II}$ is a minimum. The refocusing of the emitted light is performed correspondingly.

Additionally, the efficiency of the system can be advantageously increased by forming the tube of length portions whose diameter increases from the plasma source toward the housing. In order to provide better adaptation, the tube sections are composed of different materials, such as ceramic and metal. The tube sections are conventionally connected with one another in a gastight manner. The tube section in the lining of the melting vessel is advantageously made of ceramic and its inner diameter is advantageously between 5 and 10 mm.

It is particularly advantageous to conduct the laser beam at an acute angle along the outermost edge of the pipe and to couple the laser beam laterally by a mirror to thus obtain the least possible attenuation of the emitted light by the mirror. Beam splitters which reflect the laser light and are transmissive for the desired wavelength range of the emitted light are particularly advantageous.

According to a further feature of the invention, the optical waveguide consisting out of many filaments leading to the spectrometer is configured as a cross-section converter that is circular at the input and rectangular at the output side in arranging the filaments correspondingly.

BRIEF DESCRIPTION OF THE DRAWING

The sole FIGURE is a schematic elevational view of a preferred embodiment of the invention.

DESCRIPTION OF THE PREFERRED EMBODIMENTS

A vessel 1 provided with a refractory lining 2 and serving for the production of steel has a bore 2a below the slag level 3. A tube 4 equipped with a gas inlet nipple 5 and a quartz window 6 is received in the bore 2a and terminates at the inner wall face 2b of the lining 2. The tube section 4a extending in the lining 2 from the wall face 2b has an inner diameter of 6 mm and is composed of ceramic. The subsequent tube section 4b connected with a housing 7 is made of high-grade steel. The ceramic tube section 4a is affixed to the lining 2 and the tube section 4b by an adhesive.

Argon at a temperature of more than 500° C. is introduced into the tube 4 through the nipple 5. In the housing 7 a solid state laser beam generator 8 and optical components for guiding the laser and plasma light beams are disposed. The light of the pulsed solid state laser beam generator 8 is focused by means of a lens system 9 and mirror 10 onto the free surface 12 of the melting bath. The metal vapor plasma 11 is produced in the focal point of the laser beam.

The major part of the light emitted by the hot plasma travels past the mirror 10—which blocks only about 20% of the light exit surface—and impinges on a lens system consisting of lenses 13a and 13b which couples the light beam to an optical waveguide 14 made of quartz with cross-sectional conversion of a circular into a rectangular cross-section.

The plasma light travels through the optical waveguide 14 into a spectrograph 15 through an entrance slit 16 thereof. The spectrograph 15 is furnished with a detector system (not shown).

The detectorsystem is connected to a computer that analyses the iron line intensities $Fe_I$ and $Fe_{II}$, calculates the relation $Fe_I/Fe_{II}$ and energieses the drives 17 and 18 which move the supports of the lenses 9 and 13a synchronously the same distance until $Fe_I/Fe_{II}$ is a minimum. Then the laser light is focused at the metal surface in the bore and at the same time the plasma is focused at the input of the wave guide. The plasma is at the focal plane of lens 13a.

It will be understood that the above description of the present invention is susceptible to various modifications, changes and adaptations, and the same are intended to be comprehended within the meaning and range of equivalents of the appended claims.

What is claimed is:

1. A method of analyzing elements of a metal melt contained in a melting vessel, comprising the following steps:
    (a) introducing an inert gas at a temperature in excess of 300° C. laterally into a tube passing through a lateral wall of the melting vessel and opening thereinto;
    (b) generating a laser beam;
    (c) passing the laser beam through an adjustable first lens system;
    (d) reflecting the laser beam by a mirror into said tube through a quartz window closing said tube;
    (e) generating a plasma in said tube by focusing the laser beam by said adjustable first lens system onto the surface of the metal melt in said tube by the condition that the relation of the intensities $Me_I/Me_{II}$ is a minimum;
    (f) guiding the light generated by the plasma through said quartz window to an adjustable second lens system;
    (g) coupling the light by said second lens system with an optical waveguide so that the plasma is focused on the input end of the waveguide; and
    (h) introducing the light by the optical waveguide into a spectrometer.

2. A method as defined in claim 1, wherein said inert gas is argon.

3. A method as defined in claim 2, wherein said temperature is in excess of 500° C.

4. A method as defined in claim 1, further comprising the step of varying said adjustable first and second lens systems upon changes of wall thickness of the melting vessel, such that the laser beam continues to be focused on said surface of the metal melt and the generated plasma is focused continuously on the input end of the waveguide.

5. An apparatus for the emission spectrum analysis of a metal melt contained in a melting vessel, comprising
    (a) a housing;
    (b) a tube connected to said housing and extending therefrom and being adapted to pass through a wall of the melting vessel; the tube having an open end for communicating with the metal melt, whereby a surface of the metal melt is exposed in the tube;
    (c) a quartz window closing said tube at a distance from said open end;
    (d) a gas intake nipple provided in said tube between said open end and said quartz window for introducing an inert gas into the tube;
    (e) a laser beam generator accommodated in the housing;
    (f) a mirror supported in said housing and oriented for reflecting a laser beam, emitted by the laser beam generator, into said tube through said quartz window;
    (g) an adjustable first lens system arranged in the path of the laser beam for focusing the laser beam on the surface of the metal melt to generate a plasma thereon;
    (h) a spectrometer situated externally of said housing;
    (i) an optical waveguide extending from the housing to the spectrometer; and
    (j) an adjustable second lens system for directing light, emitted by the plasma and passing through the quartz window, into the optical waveguide for introduction therefrom into said spectrometer.

6. An apparatus as defined in claim 5, wherein said tube has two consecutive length portions of unlike diameter; the length portion closer to the housing having the greater diameter.

7. An apparatus as defined in claim 6, wherein the length portion of smaller diameter is ceramic and the length portion of greater diameter is metal.

* * * * *